US005466587A

United States Patent [19]

Fitzpatrick-McElligott et al.

[11] Patent Number: 5,466,587

[45] Date of Patent: Nov. 14, 1995

[54] METHOD FOR INTRODUCING A BIOLOGICAL SUBSTANCE INTO A TARGET

[75] Inventors: Sandra G. Fitzpatrick-McElligott, Media; John G. Lavin, Swarthmore; Germain F. Rivard, Philadelphia, all of Pa.; Shekhar Subramoney, Hockessin, Del.

[73] Assignee: E. I. Du Pont de Nemours and Company, Wilmington, Del.

[21] Appl. No.: 315,309

[22] Filed: Sep. 29, 1994

Related U.S. Application Data

[63] Continuation of Ser. No. 85,696, Jun. 30, 1993, abandoned.

[51] Int. Cl.[6] .......................... C12N 15/00; C12N 15/87

[52] U.S. Cl. .......................... 435/172.1; 435/172.3; 424/489; 424/490; 514/44; 935/52; 935/66

[58] Field of Search .......................... 800/2, DIG. 1, 800/4; 435/172.1, 172.3, 173.1–173.9, 240.1; 424/489, 490; 600/9; 935/52, 63, 85

[56] References Cited

U.S. PATENT DOCUMENTS

| | | | |
|---|---|---|---|
| 4,454,234 | 6/1984 | Czerlinski | 436/526 |
| 4,870,009 | 9/1989 | Evans et al. | 435/70 |
| 4,945,050 | 7/1990 | Sanford et al. | 435/172.1 |
| 5,149,655 | 9/1992 | McCabe et al. | 435/287 |

FOREIGN PATENT DOCUMENTS

WO91/00359 10/1991 WIPO .

OTHER PUBLICATIONS

S. Weisbrod (1982) Nature 297:289–295.

T. Matsunaga (1991) Tibtech 9:91–95.

M. Allen et al. (1992) AIP Conf. Proc. 241:176–189.

Sanford, J. C. et al., An Improved Helium–Driven Biolistic Device, *Technique*, vol. 3, No. 1, pp. 3–16, Feb. 1991.

Subramoney, S., et al., Magnetic Separation of $GdC_2$ Encapsulated In Carbon Nanoparticles, *Carbon*, vol. 32, No. 3, pp. 507–513, 1994.

Ruoff et al., Single Crystal Metals Encapsulated in Carbon Nanoparticles, *Science*, 259, 346–348, 15 Jan. 1993.

Iijima, S., Helical Microtubules of Graphitic Carbon, *Nature*, 354, 56–58, 7 Nov. 1991.

Seraphin et al., Yttrium Carbide in Nanotubes, *Nature*, 362, 503, 8 Apr. 1993.

Sanford, John C., The Biolistic Process, *Elsevier Science Publishers Ltd.*, 1067, 299–302, 1988.

Kratschmer et al., Solid C 60: A New Form of Carbon, *Nature*, 347, 354–358, 27 Sep. 1990.

Klein et al., Transformation of Microbes, Plants and Animals by Particle Bombardment, *Bio/Technology*, 10, 286–291, Mar. 1992.

Fitzpatrick–McElligott, Gene Transfer to Tumor–Infiltrating Lymphocytes and Other Mammalian Somatic Cells by Microprojectile Bombardment, *Bio/Technology*, 10, No. 9, 1036–1040, Sep. 1992.

Lavitrano, et al., Sperm Cells as Vectors for Introducing Foreign DNA into Eggs: Genetic Transformation of Mice, *Cell Press*, 57, 717–723, Jun. 2, 1989.

Whitesides, George M., et al., Magnetic Separations in Biotechnology, *Trends in Biotechnology*, 1, No. 5, 144–148, Nov./Dec. 1983.

Ebert, K. M., et al., Transgenic Farm Animals: Progress Report, *Dept. of Anatomy and Cellular Biology and Comparative Medicine, Tufts University Schools of Veterinary Medicine, Medicine and Dental Medicine*, North Grafton, Mass., 1993.

UCLA Symposium, Transgenic Models in Medicine and Agriculture, *Cellular Biochemistry*, 138, 161–185, Jan. 28–Feb. 3, 1989.

(List continued on next page.)

*Primary Examiner*—Jacqueline M. Stone
*Assistant Examiner*—Bruce Campbell

[57] ABSTRACT

A method for introducing a biological substance into a target which utilizes particles having a substantially pure carbonaceous surface to which is associated a biological substance wherein the particles are sufficiently small to penetrate the target without killing the target is described.

3 Claims, 9 Drawing Sheets

10 nm

OTHER PUBLICATIONS

Francolini, M., et al., Evidence for Nuclear Internalization of Exogenous DNA into Mammalian Sperm Cells, *Molecular Reproduction and Development,* 34, 133–139, 1993.

T. McEvoy, et al., The Expression of a Foreign Gene in Salmon Embryos, *Aquaculture,* 68, 27–37, 1988.

Gagne, Marc B., et al., Electroporation of Bovine Spermatozoa to Carry Foreign DNA in Oocytes, *Molecular Reproduction and Development,* 29, 6–15, 1991.

Wallace, Brigid M., et al., Stand and Deliver: Getting Peptide Drugs Into the Body, *Science,* 260, 912–913, 14 May 1993.

Ricks, Catherine A., Engineering of Poultry Embryos, *Conference Proceedings, Biotech USA,* Washington, D.C., 150–160, Nov. 27–29, 1990.

Lavitrano, M., et al., No Simple Solution for Making Transgenic Mice, *Cell,* 59, 239–241, Oct. 20, 1989.

Williams, B. L., et al., Production of Transgenic Farm Animals at VPI&SU: Emphasis on efficiency, *Departments of Dairy Science, Chemical Engineering Animal Science, Anaerobic Microbiology, Virginia Polytechnic Institute and State University,* Blacksburg, Va., 10–15.

Gagne, M., et al., Foreign Gene Expression in Activated Oocytes and Bovine Embryos Following pags–1acZ Plasmid Microinjection, *Theriogenology,* 39, 223, 1993.

Bosselman, et al., Germline Transmission of Exogenous Genes in the Chicken, *Science,* (Bibliographic information unknown).

Pursel, v. G., et al., Genetic Engineering of Livestock, *Science,* 244, 1281–1287, 16 Jun. 1989.

PCT Application US88/02134.

T. Matsunaga (1991) Tibtech 9: 91–95.

M. B. Gagne et al. (1991) Molecular reproduction and development 29:6–15.

S. Iijima (1991) Nature 354:56–58.

M. Allen et al. (1992) AIP Conf. Proc. 241: 176–189.

10 nm

METHOD FOR INTRODUCING A BIOLOGICAL SUBSTANCE INTO A TARGET

This is a continuation of application Ser. No. 08/085,696 filed Jun. 30, 1993, now abandoned.

FIELD OF THE INVENTION

This invention concerns a method for introducing a biological substance into a target and, in particular, to a method which utilizes particles having a substantially pure carbonaceous surface to which is associated a biological substance wherein the particles are sufficiently small to penetrate the target without killing the target.

BACKGROUND OF THE INVENTION

Biological delivery systems have long been the focus of much research due to the intense interest in introducing a variety of biological substances into a target. Such substances include nucleic acids, genetic constructs, drugs, hormones, proteins, biological stains, etc. Targets include cells, germ cells, plants, microbes, animals, organelles, tissues, etc. Diverse applications for biological delivery systems are known as is illustrated in The Pharmacological Basis of Therapeutics, Goodman and Gilman, Chapter 1, pages 1–28 (1970).

A number of delivery systems for biological substances are available. Among those options are oral ingestion, nasal sprays, pulmonary absorption, parenteral injection, transdermal or topical delivery. However, there is a desire to extend the accessibility and release (bioavailability) of a biological substance to its target. For example, genetic material can be delivered into a target. Existing technologies for introducing genetic material into living cells involve a number of systems some of which utilize biological vectors such as retroviruses or Agrobacterium to accomplish gene transfer. Others rely on chemical, e.g., calcium phosphate precipitation, polyethylene glycol, lipofection, or liposomes or physical means such as injection, microinjection or electropotation or particle bombardment to facilitate DNA transfer across cell membranes. These technologies are reviewed in Klein et al., Bio/Technology, 10: 286–291 (March 1992).

Particle bombardment also referred to as Biolistic® is a physical method for gene delivery which involves accelerating DNA-coated particles (microprojectiles) directly into cells. The Biolistic® process is described in U.S. Pat. No. 4,945,050 which issued to Sanford et al. on Jul. 31, 1990; Sanford, Biomedical Engineering: Opening New Doors, Proceedings of the 1990 Biomedical Engineering Society, Milurlecky and Clarke (Eds.) (1990); Klein et al., Bio/Technology, 10: 286–291 (March 1992). These microprojectiles must have sufficient mass to acquire the necessary kinetic energy to penetrate the particular cell sought to be penetrated and they must have integrity sufficient to withstand the physical forces inherent in the the process. The microprojectiles are described as being inert particles including ferrite crystals, gold, tungsten, spheres as well as particles of low density such as glass, polystyrene and latex beads. Biological particles can also be used. The biological substance to be transported is coated, impregnated or otherwise operably associated with solid particle to be introduced into the cell.

Particle-mediated transformation of somatic cells is described in PCT International Application having International Publication Number WO91/0035 published on Jan. 10, 1991. In this process an electric discharge particle acceleration apparatus such as the Accell® particle acceleration apparatus is used to inject very small particles of gold or other dense material carrying genetic constructs coated on them into the living cells of animals.

The ability to introduce foreign genes into the germ line and to obtain successful expression is an important aspect of genetic engineering. Such transgenic animals can be used for production of pharmaceutical proteins, disease models, improved animal health, appearance and stamina, etc.

Methods for introducing foreign genes into the germ line are limited at this time. Such methods include microinjection and retroviral transfection. Microinjection of cloned DNA directly into the pronucleus of a fertilized mouse egg has been the most widely used method for generating transgenic mice. However, the injected DNA-does not always integrate into the host genome.

One alternative considered by researchers to overcome this problem is to exploit the ability of spermatozoa to introduce foreign DNA into eggs at fertilization. Lavitrano et al., Cell 57: 717–723 (1989) purported that they were able to use sperm to transfer plasmid DNA into eggs. However, several attempts to duplicate this work have been unsuccessful to date, Brinster et al., Cell 59: 239 (1989).

Another alternative which has not been considered is the use of particle bombardment to transfer DNA directly into sperm. The method is limited because useful particles of the appropriate size for delivery into sperm have not been available. Indeed, if such particles were available then the efficiency of this method for transforming other targets of biological importance such as plants, organelles, cells, animals, organoids and tissues would be improved. In addition, the method could be extended to transform germ cells, microbes, microalgae, etc.

Recently, particles having a substantially pure carbonaceous surface were discovered in 1991 as a by-product of fullerene production, Iijima, Nature, Vol. 259, pages 56–58 (1991). Most recently, Ruoff et al., Science, Vol. 259, pages 346–348 (Jan. 15, 1993) have described novel particles in which single crystal metals were encapsulated in particles having a substantially pure carbonaceous surface. Specifically, single domain $\alpha$-$LaC_2$ small crystals were encapsulated inside particles having a substantially pure carbonaceous surface. To date no applications have been reported for these particles having a substantially pure carbonaceous surface and the like.

Surprisingly and unexpectedly, it has been found that such particles can be used not only to transform targets by means such as particle bombardment, but also such particles can be used to deliver a biological substance into a target as part of a biological delivery system. Such findings have not heretofore been reported.

SUMMARY OF THE INVENTION

This invention concerns a method for introducing a biological substance into a target which comprises (a) associating the biological substance with a particle having a substantially pure carbonaceous surface, said particle having a diameter sufficiently small to penetrate a target without killing the target, and (b) inserting the particle of step (a) into the target.

In another embodiment this invention concerns a method for introducing exogenous nucleic acid into sperm which comprises (a) accelerating a particle having a substantially pure carbonaceous surface and to which surface is associated the exogenous nucleic acid, wherein said particle encapsulates a magnetic core said particle having a diameter sufficiently small to penetrate the sperm without killing the sperm, and propelling said particles at the sperm whereby said particles penetrate the sperm; and (b) magnetically,selecting the sperm into which the particles have penetrated.

In still another embodiment this invention concerns a method for making a transgenic animal or non-human mammal which comprises (a) accelerating a particle having a substantially pure carbonaceous surface and to which surface is associated the exogenous nucleic acid, wherein said particle encapsulates a magnetic core said particle having a diameter sufficiently small to penetrate the sperm without killing the sperm, and propelling said particles at the sperm whereby said particles penetrate the sperm;

(b) magnetically selecting the sperm into which the particles have penetrated;

(c) fertilizing an egg with said magnetically selected sperm in vivo or in vitro;

(d) allowing the product of step (c) to develop to term;

wherein the product of step (d) and/or its progeny is capable of expressing the exogenous nucleic acid.

DETAILED DESCRIPTION OF THE INVENTION

Figure 1:
FIG. 1 depicts a high resolution electron microscopic image of particles having a substantially pure carbonaceous surface produced by arc-discharge.

Unless otherwise indicated, all references discussed herein are incorporated by reference.

The method of the present invention utilizes novel particles having a substantially pure carbonaceous surface to which is associated a biological substance. The particles have a diameter sufficiently small to penetrate a target without killing the target. Insertion of the particles into the target can be accomplished using any of a variety of techniques well known to those skilled in the art.

The term "carbonaceous" as used herein means composed of in part, or entirely, of carbon.

The term "substantially pure carbonaceous surface" as used herein means that the outer layers of the particle have an amount of carbon necessary to which a biological substance can associate and render the particle compatible with the target. Preferably the outer layers of the particle are greater than about 90% carbon. More preferably, the outer layers of the particle are greater than about 95% carbon. However, it is also possible that a non-carbonaceous component or components might be present in the outer layer provided that they do not interfere with association of a biological substance to the particle and they do not render the particle incompatible with the target. The substantially pure carbonaceous surface facilitates the association of a greater quantity of biological material to the carbonaceous surface. This in turn can help to increase bioavailability of the biological substance to the target.

Any particles having a substantially pure carbonaceous surface as defined herein can be used to practice the invention. Examples of suitable particles include, but are not limited to, those classified as particles having a substantially pure carbonaceous surface, particles having a substantially pure carbonaceous surface and encapsulating a dense core which can be either non-magnetic or magnetic, or fullerites (crystalline fullerenes, typically $C_{60}$–$C_{70}$) of the appropriate particle size as described in Prassides et al., Carbon, Vol. 30, pages 1277–1286 (1992).

One important aspect of these particles is that they have a substantially pure carbonaceous surface to which a biological substance can be associated. The substantially pure carbonaceous surface serves not only as a site to which a biological substance can be associated but it also renders the particles compatible with a wide variety of environments depending upon the nature of the target because the inert, non-toxic coating is compatible with the cellular milieu. In addition, biological substances including nucleic acids can be associated effectively onto the surface which in turn improves delivery of the biological substance to the target.

The size of the particles should be a size substantially smaller than that of the target sought to be penetrated. It should be small enough to penetrate the target and become incorporated into the target without killing the target. For example, the particles can be very small in the nanometer range from about 5 nm to 100 nm. However, if the particles aggregate, the aggregates can be bigger than this. For example, aggregates can range in size from about 10 nm to about 1.0 micron. Preferably, the size of the particles and any aggregate of the particles which might form will be in the range from about 5 nm to about 1.0 micron. It has been found that aggregates having sizes ranging from about 10 nm to about 1.0 micron are useful in practicing the methods of the invention.

Depending upon the means used to insert the particles into the target, it may also be necessary to consider whether it has the ability to impart sufficient kinetic energy to penetrate the desired target. When this is a consideration, the optimum particle size is small enough to produce minimal cell damage and large enough to acquire sufficient momentum, to penetrate the target; momentum being a function of size, density and velocity.

Particles having a substantially pure carbonaceous surface can be made in a variety of ways. For example, they can be made by an arc process as described in Iijima, Nature, vol. 354, pages 56–58 (1991) or chemical vapor deposition. These processes are further illustrated in the examples below. Such particles can be polyhedral or tubular in morphology having a hollow core. The density of these particles can be measured by density gradient tubes (ASTM D150556-68). The density usually exceeds about 2.0 gm/cc. FIG. 1 depicts such a particle.

Figure 2:
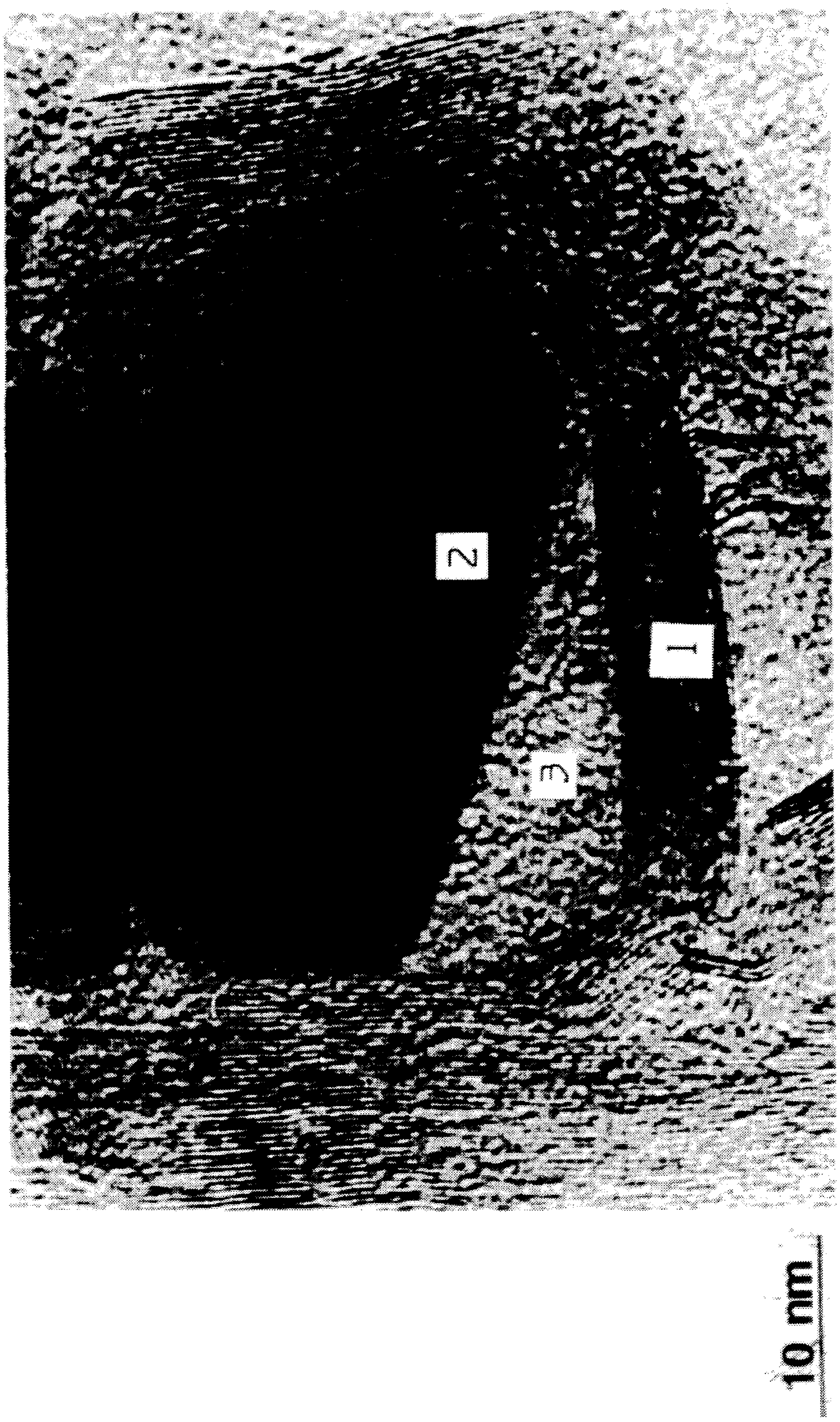
FIG. 2 depicts a high resolution electron microscopic image of a particle having a substantially pure carbonaceous surface encapsulating a dense core of α-lanthanum dicarbide.

Particles having a substantially pure carbonaceous surface and which encapsulate a dense core are similar to the particles having a substantially pure carbonaceous surface described above except that it has a dense core. Any dense material whether non-magnetic or magnetic can be used as the dense core long as it is heavier than carbon and can withstand the encapsulation process. Examples of suitable dense cores include heavy elements such as lanthanum, yttrium, copper or their carbides. An example of an α-lanthanum dicarbide encapsulated particle having a substantially pure carbonaceous surface is depicted in FIG. 2. It shows a particle having a substantially pure carbonaceous surface (1) encapsulating an α-lanthanum dicarbide crystal (2) as well as an empty region inside the particle (3). Depending upon the process used to make the particle it is possible that an empty region may not be present.

Figure 3:
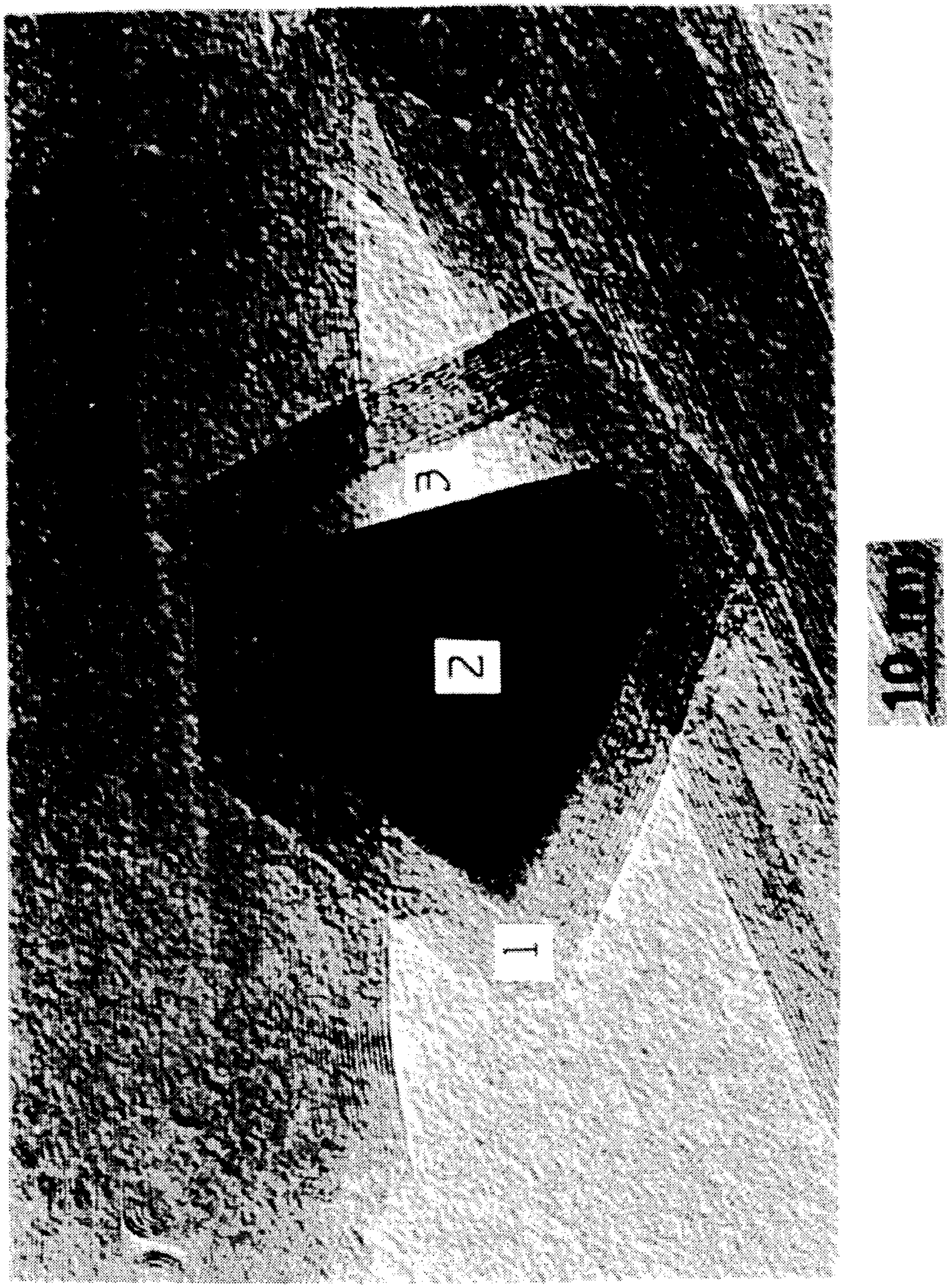
FIG. 3 depicts a high resolution electron microscopic image of a particle having substantially pure carbonaceous surface encapsulating dense magnetic material, specifically, α-gadolinium dicarbide.

Preferably, these particles having a substantially pure carbonaceous surface encapsulate a magnetic core in the form of a metal or carbide. They are similar to the particles described above except that the dense core is magnetic. Any magnetic material can be used to fill the core either partially or entirely. There can be mentioned as one example the ferromagnetic elements iron, cobalt, nickel, or gadolinium. For example, α-gadolinium dicarbide can be used. FIG. 3 shows a particle having a substantially pure carbonaceous surface (1) encapsulating an α-gadolinium dicarbide crystal (2), and a void is present adjacent to the α-gadolinium dicarbide crystal (3). Again, the void may or may not be present depending upon the process used to make the particle.

Figure 4:
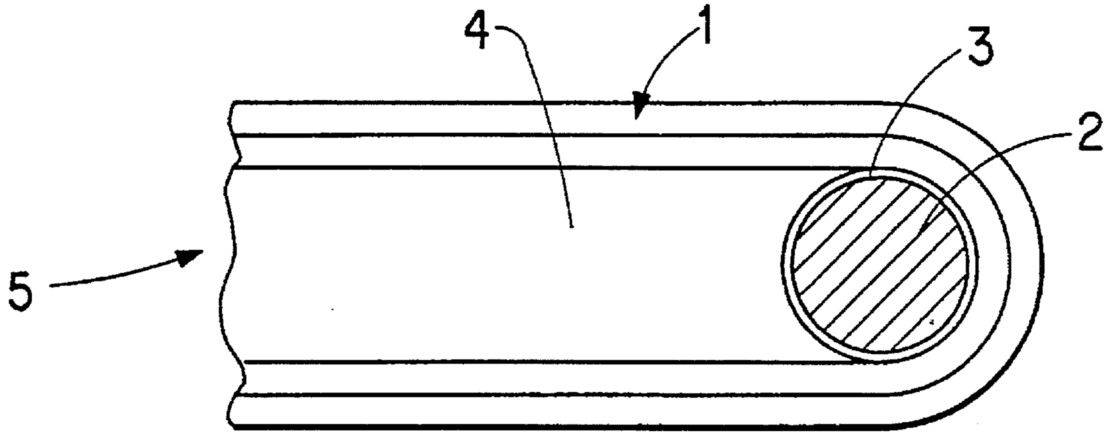
FIG. 4 is a schematic of a particle, either magnetic material or inert material coated with magnetic material, encapsulated in a particle having a substantially pure carbonaceous surface by chemical vapor deposition of carbon.

Alternatively, such a particle may be made using chemical vapor deposition as described in Example 4. In that case, the core of the particle can be a magnetic material or an inert material coated with a magnetic material. In addition, if particles are made by chemical vapor deposition, they are usually tubular in shape. An example is shown in FIG. 4. The particle having a substantially pure carbonaceous surface (1) encapsulates an inert particle (2) coated with magnetic material (3). Part of the particle may be empty (4) and one end of the particle may be open (5).

The term "associated with" as used herein means that particles can be coated, impregnated, or otherwise operably associated with a biological substance using techniques available to those skilled in the art. Examples of such techniques include adsorption, covalent attachment of the biological substance to the carbonaceous surface either directly or indirectly through the use of a suitable linking moiety, calcium precipitation, etc. DNA precipitation is described below in the Examples and in Fitzpatrick-McElligott, Bio/Technology, 10(9): 1036–1040 (September 1992).

Examples of biological substances which can be associated with the particles having a substantially pure carbonaceous surface include, but are not limited to, nucleic acids, genetic constructs, proteins such as enzymes, toxins, pharmaceutical compounds, viruses, hormones, lipids, biological stains, organelles, and vesicles. Preferably, the genetic construct should code for a protein with effective flanking regulatory sequences to express the protein in the target. It is also possible to use a genetic construct which is an RNA strand or DNA sequence effective to inhibit a native gene or to retard a disease process. DNA or RNA sequences and their derivatives which inhibit gene expression can also be referred to as antisense.

Examples of targets into which the particles can be inserted include, but are not limited to, cells, germ cells such as sperm. There can also be mentioned microbes, microalgae, plants, organelles, cells, animals, organoids, organs and tissues. "Organoids" are organ-like structures of clusters of cells or tissues which can be created in an in vitro culture and surgically re-implanted into a living animal. Such organoid cultures may be used effectively with mammals, and in humans to reintroduce transformed somatic cells back into a patient for genetic therapy or other therapeutic use. Examples of microbes include bacteria, fungi, viruses, etc. Examples of microalgae include chlorella, chlamydomonas, etc. Examples of organelles include nucleic, mitochondria, chloroplasts, etc.

The particles having a substantially pure carbonaceous surface to which is associated a biological substance can be inserted into a target using any number of means available to those skilled in the art. There can be mentioned direct parenteral injection such as intramuscular, intravenous and subcutaneous. There can also be mentioned nasal sprays and implants as well as microinjection.

The preferred means by which to insert these particles into a target is by particle bombardment also referred to as Biolistic®. This technique involves accelerating particles to which is associated a biological substance directly into a target. Particle acceleration constitutes the subject matter of U.S. Pat. No. 4,945,050 which issued on Jul. 31, 1990 to Sanford et al. Particles e.g., microprojectiles, can be used to transfer genes to a broad range of tissues, cells and organelles in many different species. Several acceleration methods such as gun-powder, electric discharge, and gas-power are available to deliver particles through membranes, cell walls, extracellular matrices, etc. A helium-driven acceleration system has been developed and is described in Sanford et al., Technique 3:3–16 (1991).

The efficiency of gene transfer by physical means and, in particular, by particle bombardment is greatly improved by using particles encapsulating a dense core which increases cell penetration. Furthermore, the inert, non-toxic substantially pure carbonaceous surface is compatible with the cellular milieu. Because biological substances including nucleic acids can be associated effectively onto the surface, delivery of such substances into a target is improved.

In another embodiment this invention concerns a method for introducing exogenous nucleic acid into sperm which comprises (a) accelerating a particle having a substantially pure carbonaceous surface and to which surface is associated the exogenous nucleic acid, wherein said particle encapsulates a magnetic core said particle having a diameter sufficiently small to penetrate the sperm without killing the sperm, and propelling said particles at the sperm whereby said particles penetrate the sperm; and (b) magnetically selecting the sperm into which the particles have penetrated.

The introduction of exogenous nucleic acid into sperm using the method of the invention offers many advantages. Not the least of which is the simplicity of using such sperm for artificial insemination and allowing in vivo development of the embryo. The use of sperm as vectors for insertion of foreign nucleic acids will facilitate gene integration into the genome.

The method of the invention is a simple, straight-forward approach for introducing exogenous nucleic acids into sperm. This method constitutes a major advance over the methods currently available because extensive training is not required.

By inserting particles having a substantially pure carbonaceous surface which encapsulates a magnetic core into sperm, a physical means is provided by which to select the sperm containing these particles. Magnetic sorting of sperm after particle bombardment as described in Example 9 below provides a means for enriching the population of sperm carrying the desired exogenous nucleic acids.

In still another embodiment, the method of this invention can be used to make a transgenic animal or non-human mammal which comprises (a) accelerating a particle having a substantially pure carbonaceous surface and to which surface is associated the exogenous nucleic acid, wherein said particle encapsulates a magnetic core said particle having a diameter sufficiently small to penetrate the sperm without killing the sperm, and propelling said particles at the sperm whereby said particles penetrate the sperm;

(b) magnetically selecting the sperm into which the particles have penetrated;

(c) fertilizing an egg with said magnetically selected sperm in vivo or in vitro;

(d) allowing the product of step (c) to develop to term;

wherein the product of step (d) and/or its progeny is capable of expressing the exogenous nucleic acid.

The introduction of foreign genes into the germ line of animals and the successful expression of the inserted gene are major technological advances in the field of biology. Transgenic animals provide a means to produce economically important proteins in milk, blood, eggs, etc. Moreover, such animals can be used to provide tissue for medical transplantation. Transgenic technology offers exciting possibilities for generating precise animal models for human diseases. One commonly used technique for introducing genes into embryos is the direct microinjection of recombinant DNA into the pronucleus of fertilized eggs. This method is tedious, inefficient, requires extensive training and expensive equipment. Such methods require removal of the eggs and in vitro culture of the developing embryo.

Infection of mouse embryos and embryonic stem cells with retrovirus constitutes another method for genetically manipulating embryos. The main disadvantages of the use of retroviruses for gene transfer are the size limitation for transduced DNA and the risk of using retrovirus as a means for gene insertion. Such disadvantages are overcome using the method of the invention.

Techniques for in vitro and in vivo development of fertilized eggs are well known to those skilled in the art.

The following examples are intended to illustrate the invention and are not to be construed as limitations thereon.

EXAMPLE 1

Particles Having a Substantially Pure Carbonaceous Surface

Figure 5:
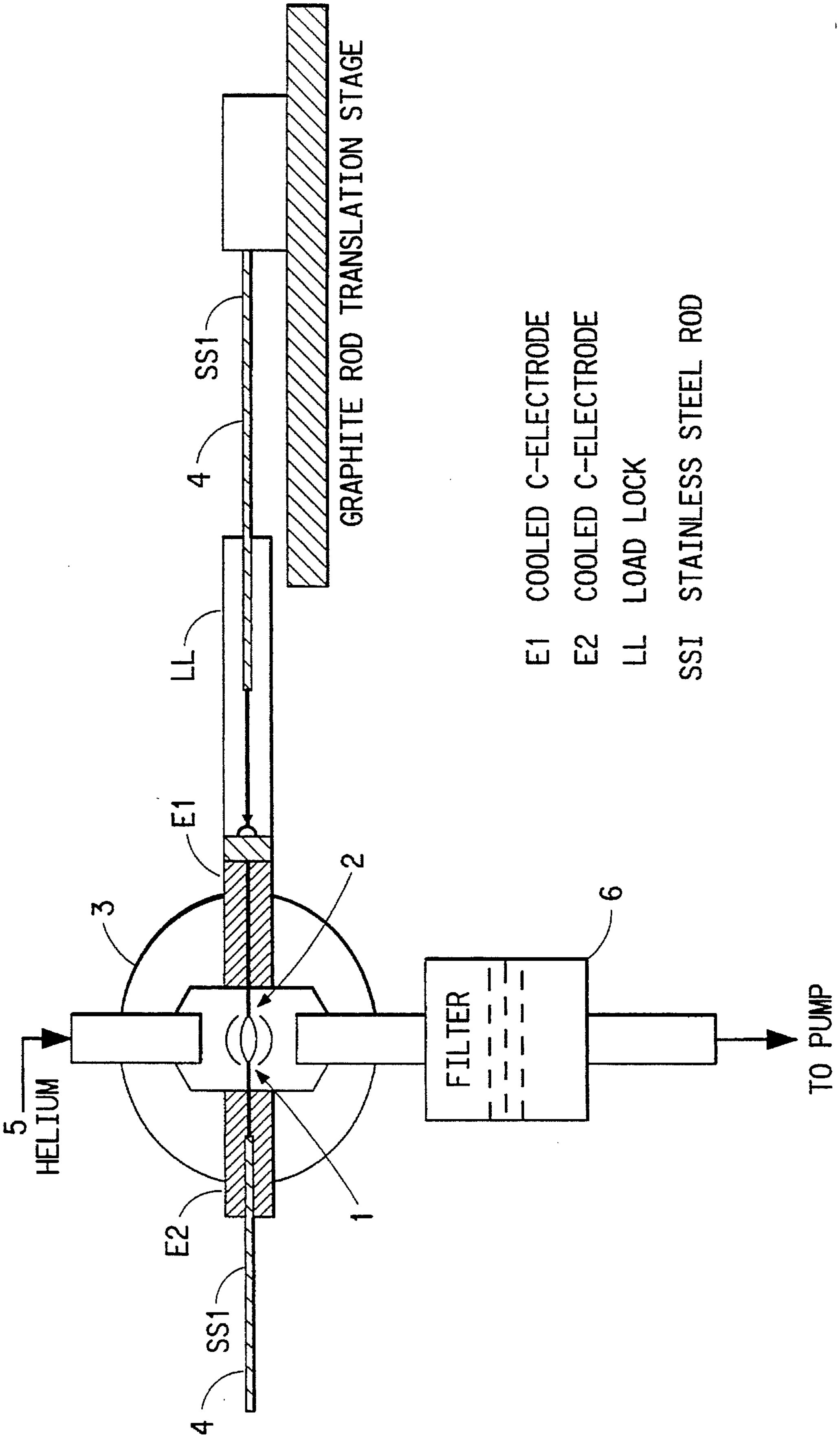
FIG. 5 is a schematic of an apparatus for conducting arc-discharge experiments to produce particles having a substantially pure carbonaceous surface.

Nanometer scale carbonaceous polyhedra and tubes were first discovered in 1991, as a by-product of fullerene production as described in Iijima, Nature, vol. 354, pages 56–58 (1991). The apparatus for the synthesis of particles having a substantially pure carbonaceous surface, in the diameter range of 5 to 20 nm, and carbonaceous nanotubes, typically 5–30 nm in diameter and 1–2 μm in length, is very similar to the one used for the mass production of $C_{60}$ as is described by Kratschmer et al. in Nature, vol. 347, pages 354–358 (1990) and is depicted in FIG. 5. It consists of two carbon electrodes (1 and 2), a chamber to maintain the inert gas at a fixed pressure (3), stainless steel rods to position the two electrodes (4), a source of inert gas attached to the chamber (5), a DC current generator (not shown), and a filter and pump arrangement to collect the soot (6). The variable factors are anode (positive electrode)—cathode (negative electrode) gap distance, current at which the arc-discharge experiment is run, voltage (potential difference) between the electrodes, and pressure of inert atmosphere.

The carbon arc-discharge experiments are carried out in a controlled pressure reaction vessel, using a voltage typically in the 18–20 volt range. A typical anode (positive electrode) diameter is 6–8 mm, and it is usually about 30 cm long.

A typical cathode (negative electrode) diameter is 9–13 mm. Cathode diameter is always higher than anode diameter.

Inert gas (either He or Ar) is flowed through the reaction vessel at constant pressure between 100 and 1,000 torr.

The electric current between the electrodes depends on factors such as electrode diameter, gap between electrodes, and inert gas pressure, but can be typically adjusted between 50 and 125 amps.

A computer-controlled motor which adjusts the position of the anode with respect to the cathode is used to obtain a gap distance of 1 mm, and this step initiates the arc-discharge process. During the experiment, the anode is continuously consumed, and a "boule" or "volcano" grows on the cathode. The computer controlled motor ensures that the gap distance between the remaining anode and the tip of the growing boule is maintained at 1 mm.

Figure 6:
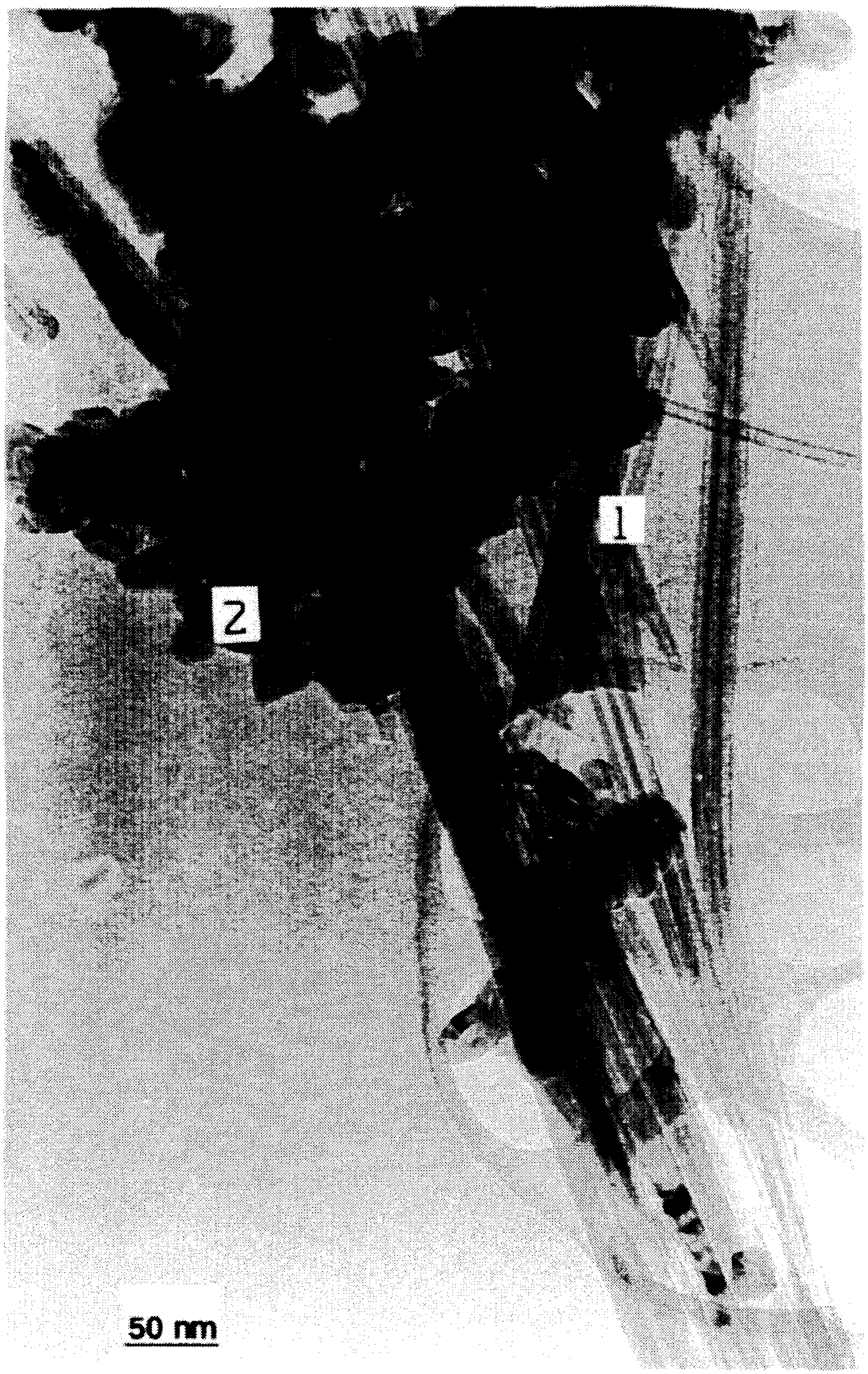
FIG. 6 is a low resolution electron microscopic image of a product of an arc-discharge experiment.

The particles having a substantially pure carbonaceous surface are present in the core region of the boule or growth at the end of the cathode. The core region is extracted by means of a sharp pointed tool, and the extract is ground and dispersed in ethanol by ultrasonic means. The dispersed solution is placed on carbon coated electron microscopy grids to facilitate structural analysis. A typical transmission electron microscopic bright-field image is shown in FIG. 6, which depicts the morphologies of particles having a substantially pure carbonaceous surface (tubes) (1) and (polyhedra) (2). FIG. 1 shows a high resolution image of particles having a substantially pure carbonaceous surface.

EXAMPLE 2

Particles Having a Substantially Pure Carbonaceous Surface Encapsulating A Dense Core Dense core encapsulated particles having a substantially pure carbonaceous surface in the diameter range of 20 to 50 nm can be produced incorporating electro-positive elements as described in Ruoff et al., Science, vol. 259, pages 346–348 (1993). The apparatus and experimental procedure are similar to those used for processing the particles described in Example 1 above. The following example is shown for α-lanthanum dicarbide (α-$LaC_2$).

A graphite anode which is 7.9 mm in diameter and 30.5 cm in length is drilled to a depth of 23.0 cm using a 3.2 mm drill.

The cavity in the anode is packed with $La_2O_3$. Weighing of the rod prior to and after packing with $La_2O_3$ provides a La:C molar ratio of approximately 0.02.

A graphite cathode is 12.7 mm in diameter. Anode to cathode gap distance is maintained at 1 mm using the computer controlled motor drive for positioning the anode.

The carbon arc conditions include a DC current of 150 amps, potential difference between anode and cathode of 18 volts, and a helium pressure of 500 torr.

A typical high resolution transmission electron microscopic image of $\alpha$-$LaC_2$ encapsulated particle having a substantially pure carbonaceous surface, produced as a result of the arc-discharge experiment using a $La_2O_3$ filled anode, is shown in FIG. 2.

EXAMPLE 3

Particles Having a Substantially Pure Carbonaceous Surface Encapsulating A Dense Core Which Is Magnetic Dense core encapsulated particles having a substantially pure carbonaceous surface with diameters ranging from 20 to 50 nm can be produced where the dense core of the particle is magnetic and amenable to preferential separation using either a permanent or electro-magnet. The apparatus and experimental procedure are similar to those used for synthesizing any dense core encapsulated particles having a substantially pure carbonaceous surface as described in Example 2 above. The following example is shown for $\alpha$-gadolinium dicarbide ($\alpha$-$GdC_2$), a magnetic material with a Curie temperature of 293K.

A graphite anode which is 7.9 mm in diameter and 30.5 cm in length is drilled to a depth of 23.0 cm using a 3.2 mm drill. The cavity of the anode is packed with $Gd_2O_3$. Weighing of the rod prior to and after packing with $Gd_2O_3$ provides a Gd:C molar ratio of approximately 0.02. Pure gadolinium (Gd) metal can also be used in the anode. Weighing of the rod prior to and after packing with Gd provides a Gd:C molar ratio of approximately 0.08.

Graphite cathode is 12.7 mm in diameter. The anode to cathode gap distance is maintained between 2 and 5 mm with $Gd_2O_3$ in the anode using a computer controlled motor drive for positioning the anode. With pure Gd in the anode, the anode to cathode gap distance is maintained between 2 and 8 mm. With $Gd_2O_3$ in the anode, the carbon arc conditions include a DC current of 75 amps, potential difference between anode and cathode of 18 volts, and a helium pressure of 1,000 torr. With pure Gd in the anode, the carbon arc conditions include a DC current of 75 amps, potential difference between anode and cathode of 18 volts, and a helium pressure of 500 torr.

A typical high resolution transmission electron microscopic image of single crystal $\alpha$-$GdC_2$ encapsulated particles having a substantially pure carbonaceous surface is shown in FIG. 3. This particle was produced as a result of the arc-discharge experiment using pure Gd in the graphite anode.

Since $\alpha$-$GdC_2$ is magnetic, particles having a substantially pure carbonaceous surface encapsulating this dense, magnetic core can be preferentially separated using a powerful permanent magnet like samarium cobalt or a high field strength electromagnet at room temperature.

EXAMPLE 4

Preparation of Particles With A Substantially Pure Carbonaceous Surface Encapsulating A Dense, Magnetic Core The method described in this example is based on the methods described in U.S. Pat. No. 4,663,230 issued to Tennent on May 5, 1987, the disclosure of which is hereby incorporated by reference.

Catalyst is prepared by placing 10 gm of Davison SMR-37-1534 SRA alumina powder into a 4 oz wide mouth glass jar containing a stirring rod. While stirring the powder, 0.81M $Fe(NO_3)_3$ is added dropwise to the point of incipient wetness; 4.1 mL is required. The powder is heated in the jar on a hot plate until dry, the temperature being kept below the level at which NOx is evolved. The catalyst is then ultrasonically dispersed in water and transferred to a ceramic boat, which is placed in the center of a 1 inch mullite tube in an electric furnace at room temperature. The furnace temperature is raised from room temperature to 500° C. over 15 minutes and maintained at 500° C. under air for 1 hour. The reactor is then briefly purged with argon at 300 mL/min (flow rates for all of the different gases used in this process, and described below, are the same). The temperature is then raised to 900° C. over 15 minutes under hydrogen flow and held at this level for 60 minutes under the same hydrogen flow. The temperature is then raised to 1100° C. over 10 minutes, maintaining the same hydrogen flow. Gas flow is then switched to benzene-saturated hydrogen obtained by bubbling hydrogen through benzene at 20° C. (approximately 9 parts of hydrogen per part of benzene). Flow is maintained for 10 seconds, and then the gas is switched to argon. The furnace is then cooled to room temperature and the particles having a substantially pure carbonaceous surface are scraped out of the boat.

EXAMPLE 5

Preparation of DNA-Coated Particles Having a Substantially Pure Carbonaceous Surface Encapsulating a Dense, Magnetic Core Sixty milligrams of particles having a substantially pure carbonaceous surface encapsulating a dense, magnetic core($\alpha$-$GdC_2$) made using the protocol described in Example 3 above are added to a microfuge tube with 100 µl of 70% or 100% ethanol vortexed for 3–5 minutes and soaked for 15 minutes. The particles are spun in a microfuge for 1 minute. The ethanol is removed and the pellet washed three times in sterile distilled water. At this stage the particles can be stored in sterile 50% glycerol at a concentration of 60 mg/ml. Immediately before use, the mixture is vortexed for five minutes and an aliquot of 50 µl of the particles is removed.

Plasmid DNA is precipitated onto the particles having a susbstantially pure carbonaceous surface encapsulating $\alpha$-$GdC_2$ by adding to the mixture 50 µl of calcium chloride, 20 µl of spermidine (free base; tissue culture grade, Sigma Chemical Co., St. Louis, Mo.) while vortexing vigorously. Continue vortexing for 2–3 minutes. After incubating for one minute, the particles are pelleted by centrifugation at 12,000 RPM (Sorvall Microspin 12S) for two seconds. The supernatant is removed and discarded. The pellet of particles is washed gently in 70% ethanol and the liquid supernatant is discarded. Again the particles are washed in a 140 µl of 100% ethanol, and liquid is discarded. Next 48 µl of 100% ethanol is added. The particles having a substantially pure carbonaceous surface are resuspended by vortexing at slow speeds for 2–3 minutes. The ethanol/DNA-coated particle mixture (6 μl) is spread evenly onto the center of the 2.4 cm Kapton® disk with the pipette tip. The disks are then dried in a dessicator.

RESULTS

Figure 7:
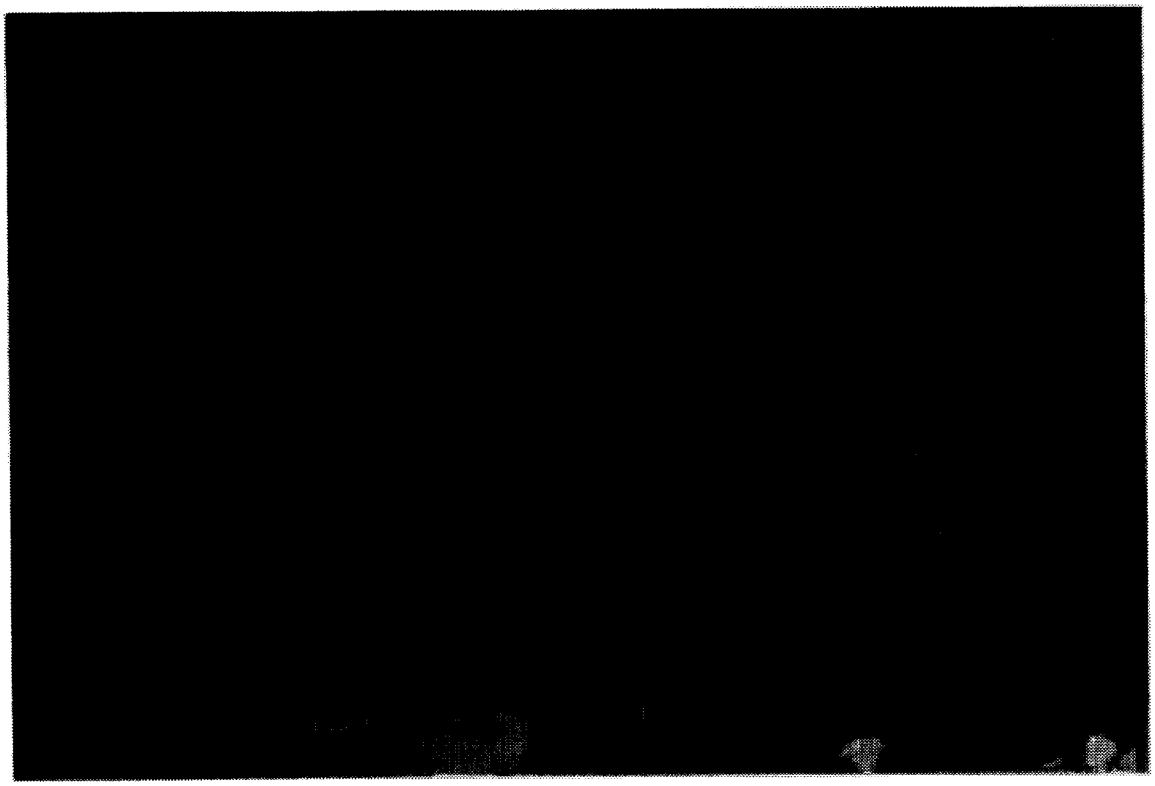
FIG. 7 depicts particles having a substantially pure carbonaceous surface encapsulating α-gadolinium dicarbide to which have been associated fluorescent DNA.

The results are shown in FIG. 7. DNA— coating on the particles having a substantially pure carbonaceous surface encapsulating a magnetic core are shown using a fluorescent dye, propidium iodide. These particles and their aggregates coat more efficiently with DNA than gold or tungsten particles typically used for particle bombardment and, thus, carry more DNA into the targets.

EXAMPLE 6

Particle Acceleration Methods

Particles can be accelerated into the target by a number of mechanisms. These methods include centripetal force such as vortexing, and centrifugation, electric discharge, gun powder and compressed air.

Particle Delivery System

Figure 8:
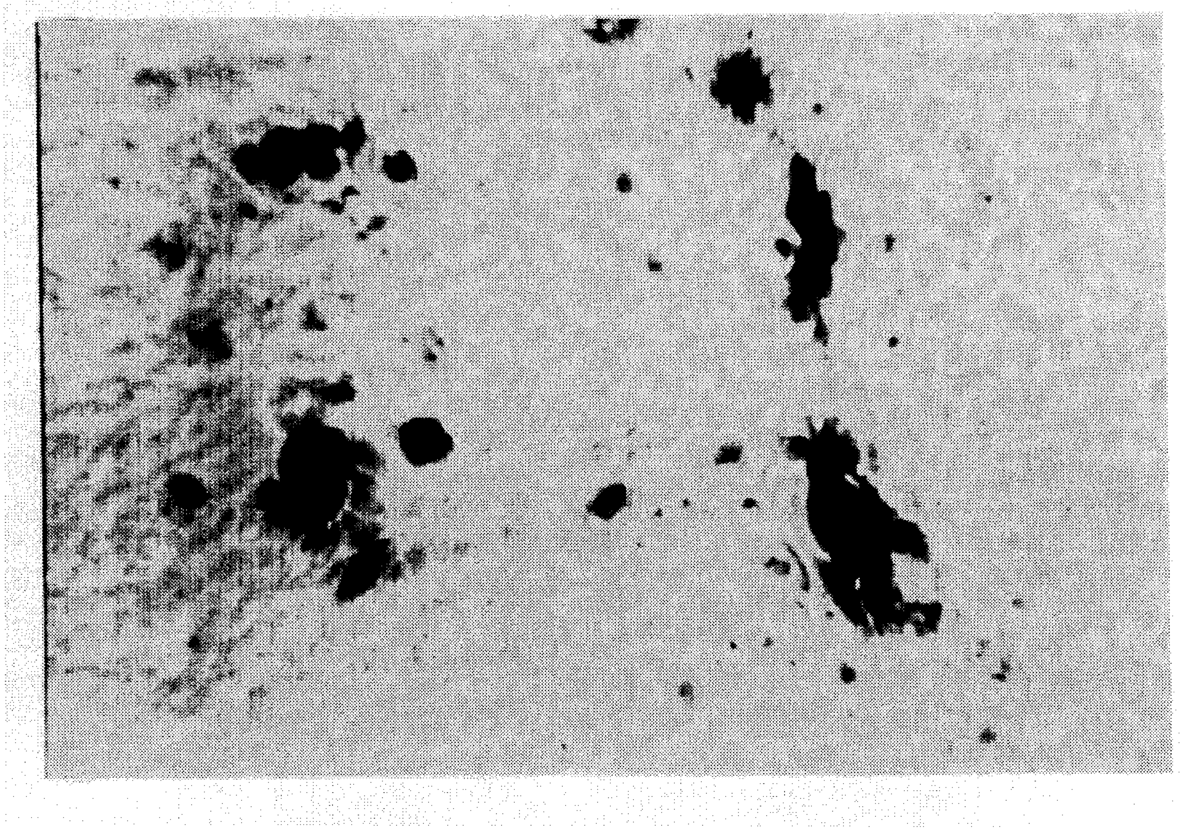
FIG. 8 depicts gene expression in an animal ovary cell line after particle bombardment with particles having substantially pure carbonaceous surface and encapsulating α-gadolinium dicarbide to which has been associated plasmid DNA containing the lac z coding region.

The Biolistic® helium powered PDS-1000/He (Bio Rad, Richmond, Calif.) is used for these experiments on animal cells in vitro (FIG. 8). Gas-shockwaves generated by pressurized helium gas accelerate the particles having a carbonaceous surface and encapsulating a dense core to high velocities. The particles described, carrying precipitated DNA, are spread onto a thin Kapton® disk (macrocarrier: 2.4 cm in diameter). This disk is held in place about 1 cm from a stopping screen. The helium is retained until the preselected pressure (2000 psi for animal cells) is reached by rupture disks. At this point, the rupture disks (stack of Kapton disks 1.3 cm in diameter) are broken and the gas shockwave propels the macrocarrier containing the DNA-coated particles described above. The impact of the macrocarrier onto the wire-mesh screen stops the disk but the particles proceed with their DNA-coating into the sample-containing petri dish. Penetration by the particles having a substantially pure carbonaceous surface encapsulating a dense core into the target (microbes microalgae, plants, animals, tissues, organs, organelles or cells) occurs within the sterile vacuum chamber. Pressure of the helium gas, the level of the tissue within the chamber, and the vacuum pressure within the chamber, control the impact velocity of the particles.

Results

The size and density of the dense core particles having a substantially pure carbonaceous surface improves the efficiency of cell penetration with these acceleration methods. The particles having a substantially pure carbonaceous surface encapsulating a dense core and to which a biological substance can be associated offer an advantage for penetration of smaller cells and organelles; sperm, microbes, microalgae, nuclei, mitochondria. Moreover the carbonaceous coating improves the association of biological substances to the surface of the particle and their aggregates.

EXAMPLE 7

Introduction of Exogenous Genetic Substance into Animal Cells

DNA-coated particles are prepared as described in Example 5 above. The plasmid DNA construction used for this experiment and coated on the particles having a substantially pure carbonaceous surface encapsulating a magnetic core was purchased from Pharmacia (Piscataway, N.J.). The plasmid (pCH110) consists of the SV-40 promoter and the lac z coding region.

Animal Cell Preparation

Throughout the growth and bombardment procedures, the cells were kept under sterile conditions. CHO (Chinese hamster ovary cells) were grown according to established conditions almost to confluency in plastic petri dishes. In general cells are more efficiently transformed while attached to a substrate. CHO cells attach directly on to the plastic dishes. Cells that normally grow in suspension culture are attached for these protocols to the plastic petri dishes with Cell Tak (Collaborative Biomedical Products, Becton Dickinson Labware Bedford, Mass.). Most of the growth medium is removed from the petri dish before placement in the sterilized vacuum chamber.

In Vitro Bombardment

The cells are placed 3 cm from the microcarrier launch assembly. The chamber is evacuated to a level of 15 in. Hg before bombardment. Within fifteen minutes after bombardment, the media is replaced, the dish covered and placed in a humidified, $CO_2$ incubator at temperatures appropriate for the cell type ca. 37° C. Cell Culture/Cell Viability EL4 (T-lymphocyte cells developed from cultures of MRL-lpr/lpr spleen) (Fox et al., J. of Biological Response Modifiers, 9: 499–511 (1990)), and BF-1 (IL2 dependent T-lymphocyte cell from adenocarcinoma) are cultured in 5% $CO_2$ in RPMI (Gibco) containing 0.1 mM nonessential amino acids, 0.1M sodium pyruvate, 2 mM L-glutamine, and 100 g of gentamicin sulfate. The media is supplemented with 50 m 2-mercaptoethanol (Aldrich) and 10% fetal bovine serum (Gibco). Growing cells are trypsinized and replated at $1\times10^5$ cells per petri dish. Four days after incubation the cultures were ready for bombardment. CHO and EL4 cells attached directly to the plastic dish but the BF1 cells were attached for bombardment with Cell Tak. Cell viability, following bombardment, was estimated using the trypan blue exclusion test.

Transient Expression Assays

Histochemical staining to reveal the expression of the marker gene (β-galactosidase (EC3.2.1.23)) is performed 48 hours after bombardment. To detect the β-galactosidase transformed cells, the petri plates are washed three times in Tris-buffered saline. The cells are fixed for 5 minutes in 0.5% (vol/vol) glutaraldehyde in phosphate buffered saline (PBS) washed three times in PBS and then stained at 37° C. with X-gal (5-bromo-4-chloro-3-indoyl-6-D-galactopyranoside (Price et al., Proc. Natl. Acad. Sci. (USA), 84:156–160 (1987)). Transformed cells and clones develop a deep blue stain in 3–6 hours. A dense precipitate appear in these cells after reacting the transferred enzyme with an exogenous substrate and the resulting products catalyze a colored precipitate. Control cultures (bombarded without plasmid DNA) do not result in any detectable cellular staining when placed in the enzyme assay solutions. Reporter gene expression efficiencies are determined by counting the number of stained and unstained cells in a hemacytometer. The central 30 mm diameter area of the dish is selected for evaluation.

RESULTS

The results are shown in FIG. 8. Mammalian cells (Chinese Hamster Ovary cells) show gene expression (blue stain) after bombardment with DNA-coated particles having a substantially pure carbonaceous surface encapsulating a magnetic core. The plasmid DNA containing the coding region for the lac-z gene is associated with the surface of these particles.

EXAMPLE 8

Introduction Of Biological Material Into Sperm By Particle Acceleration

Bovine sperm are prepared by thawing the frozen straws in a water bath (37° C.) for 30 seconds. The sperm are then washed twice in sperm-TALP solution (Parrish et al., Biology of Reproduction, 38: 1171–1180 (1988). Next the sperm are resuspended at $10\times10^6$ sperm per ml in sperm-TALP. Sperm suspensions are enriched for live motile sperm by a "swim-up" protocol (Parrish et al., Theriogenology 25:591–600 (1986)). Sperm motility is then checked under a microscope in order to determine their viability. The sperm are then transiently attached to the surface by placing 200 µl of diluted sperm ($1\times10^5$) in Cell-Tak coated petri dishes (15 mm in size).

Prior to bombardment the particles are coated with the DNA precipitation method of Example 5 above. These particles are dispersed in ethanol and loaded by spreading onto a Kapton disk which is allowed to dry in a dessicated area. The particle loaded disk is then placed in the instrument and the appropriate stopping screens and pressure disks are inserted as described in the instruction manual for the Biolistic particle delivery technology (Bio Rad Ca.). Although several Helium pressures, vacuum pressure and target distance levels can be used, higher velocities give better results in penetration of sperm cells. High helium pressures (1500–2500 psi), target distances closer to the acceleration device (3 cm) and high vacuum pressure (20 in Hg) are selected for insertion of the particles having a substantially pure carbonaceous surface encapsulating a dense, magnetic core.

Sorting Sperm containing Particles Having a Substantially Pure Carbonaceous Surface Encapsulating A Dense, Magnetic Core After bombardment the sperm are rinsed carefully from the plates, pooled and resuspended in sperm-TALP solution. Next the sperm is washed twice in sperm-TALP (1100 RPM for 10 minutes). In order to separate the live motile sperm from the damaged sperm and particles, the "swim-up" method is used (Parrish et al Theriogenology 25:591–600, 1986). Viable, motile sperm in 1 ml aliquots are gently shaken in a glass tube (Corning 10 mm×75 mm). The tube is then placed in an electromagnetic field such that the lower section of the tube is subject to the magnetic force (20,000 Gauss). The fluid in the upper portion of the tube containing sperm-without-magnetic particles is aspirated gently. The remaining sperm-with-particles are resuspended and an aliquot counted and observed under the microscope. The sperm concentration is adjusted to $25\times10^6$ per ml.

Results

Figure 9:
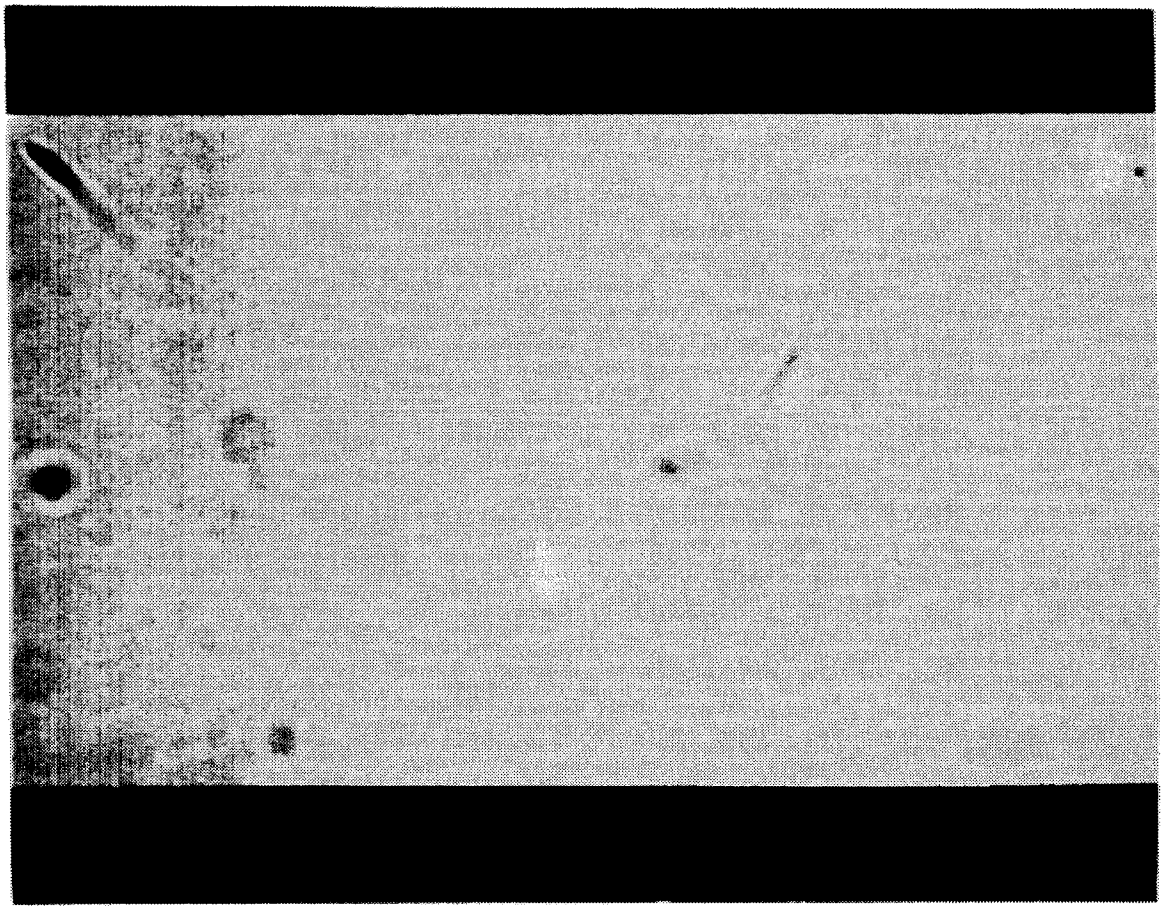
FIG. 9 depicts bovine sperm containing particles having a substantially pure carbonaceous surface and encapsulating α-gadolinium dicarbide to which has been associated fluorescently-labelled DNA. The particles were inserted using particle bombardment.

The results in FIG. 9 show mammalian sperm before magnet sorting. Some sperm contain particles with fluorescently labelled DNA and other sperm do not contain particles with fluorescently labelled DNA. Since the particles encapsulate a magnetic core, sorting with a magnet will separate the sperm containing such particles from those sperm not containing the particles.

EXAMPLE 9

In Vitro Fertilization With Magnetically Sorted Sperm

Oocyte Maturation

The ovaries are collected and stored at 34°– 37° C. in 0.9% phosphate buffered saline. Next the primary oocytes are aspirated from the follicles (2–8 mm) using 18G needle, allowed to settle in a 15 ml tube. Intact cumulus-oocyte complexes are selected and are washed three times in Lb-TALP supplemented with 10% heat-treated fetal calf serum. Ten cumulus-oocyte complexes are placed in 50 µl droplets of in vitro maturation medium consisting of a 2 ml solution of TCM- 199, 10% fetal bovine serum, 20 µg pyruvate, 10 µg lutenizing hormone, 1 µg follicle stimulating hormone, and 5 µl gentamycin under mineral oil. The oocytes are allowed to mature for 20–24 hours in a humidified $CO_2$ incubator at 39° C. (5% $CO_2$ in air). Next the oocytes are transferred to Fert-TALP (Parrish et al., Biology of Reproduction, 38: 1171–1180 (1988).

In Vitro Fertilization

At a concentration of $25\times10^6$, 2 µl of magnetically sorted sperm-containing particles are added to the cumulus-oocyte complexes (10 oocytes) in a volume of 45 µl droplets. The droplets contain Fert-TALP supplemented with 2 µl heparin and 2 µl of PHE solution which is 10 µM penicillamine, 1 µM hypotaurine, and 25 µM epinephrine. The media and mineral oil (Aldrich Milwaukee, Wis.) are preexposed to the maturation conditions for a minimum of 2 hours. The fertilized cumulus-oocyte complexes are incubated in fertilization media for 12–18 hours at 39° C. in a humidified $CO_2$ incubator (5% $CO_2$ in air). The resulting zygotes are transferred in in vitro growth droplets (TCM 199, 10% fetal bovine serum, and 50 µg/ml gentamycin).

Initial cleavage was assessed 42 hours after adding sperm. Normal development was assessed by counting the number of newly formed two-cell embryos with visible nucleoli.

Results

The results presented in Table 1 below show that the fertilization rate with sperm containing particles is assessed at 75% and 66.6% by counting the number of fertilization droplets containing two-cell stage embryos. The percentage of two-cell embryos are 19% and 15% after fertilization with sperm containing particles having a substantially pure carbonaceous surface encapsulating a magnetic core.

TABLE 1

Fertilization Rate of Sperm with Particles Having a Substantially Pure Carbonaceous Surface

| Fertilization Rate | Control Sperm without particles[1] | Experimental Sperm with particles[1] |
|---|---|---|
| % Dividing embryos | 66.6% | 75% |
| per droplet | 100% | 66.6% |
| % | 9% | 19% |
| Dividing embryos | 43% | 15% |

[1]Particles having a substantially pure carbonaceous surface encapsulating a magnetic core.

EXAMPLE 10

Embryo Transfer

Recipient cows are synchronized in their estrous cycle. Embryos are transferred non-surgically to recipient heifers 5–7 days after estrous day (1–2 embryos per uterine horn). Pregnancy is determined by rectal palpation at 45 to 60 days of gestation.

Artificial Insemination With Sperm Containing DNA-Coated Particles Having a Substantially Pure Carbonaceous Surface Encapsulating a Magnetic Core Recipient cows are artificially inseminated with magnetically sorted sperm containing DNA-coated particles having a substantially pure carbonaceous surface using procedures as described in Reproduction in Farm Animals (Hafez (ed.)) (1960). Calves are assayed for the transgene, after birth. The casein-hLF gene (Krimpenfort et al. Bio/Technology 1991) is used for casein signal sequence and flanked by the 5' and 3' untranslated regions of the bovine casein gene. The introns are included since they have been shown to increase expression. The transgene expression is assayed in the ear tissue of the calf or mammary gland of the adult animals.

What is claimed is:

1. A method for introducing a biological substance into a biological target which comprises:

(a) adsorbing the biological substance onto a particle encapsulating a dense metallic core and having a substantially pure carbonaceous surface, said particle having a size sufficiently small to penetrate a target without rendering the target non-functional, said biological substance selected from the group consisting of nucleic acids, genetic constructs, and proteins, said biological target being selected from the group consisting of germ cells, microbes, microalgae, plants, organelles, cells, animals, organoids, and tissues, and (b) inserting the particle of step(a) into the target by accelerating the particle and propelling the particle at the target whereby said particle penetrates the target.

2. A method according to claim 1 wherein the genetic construct codes for a protein and has effective flanking regulatory sequences to express the protein in the target.

3. A method according to claim 1 wherein the dense metallic core is magnetic.

* * * * *